United States Patent
Stork et al.

(10) Patent No.: US 9,688,650 B2
(45) Date of Patent: *Jun. 27, 2017

(54) METHOD FOR PRODUCING 2-SUBSTITUTED 4-HYDROXY-4-METHYL-TETRAHYDROPYRANS IN A REACTOR CASCADE

(71) Applicant: BASF SE, Ludwigshafen (DE)

(72) Inventors: Timon Stork, Mannheim (DE); Karl Beck, Östringen (DE); Klaus Ebel, Heddesheim (DE); Oliver Bey, Niederkirchen (DE); Gabriele Gralla, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/787,285

(22) PCT Filed: Apr. 28, 2014

(86) PCT No.: PCT/EP2014/058538
§ 371 (c)(1),
(2) Date: Oct. 27, 2015

(87) PCT Pub. No.: WO2014/177486
PCT Pub. Date: Nov. 6, 2014

(65) Prior Publication Data
US 2016/0068500 A1 Mar. 10, 2016

(30) Foreign Application Priority Data
Apr. 29, 2013 (EP) .................................. 13165767

(51) Int. Cl.
*C07D 321/00* (2006.01)
*C07D 315/00* (2006.01)
*C07D 309/10* (2006.01)

(52) U.S. Cl.
CPC .................................. *C07D 309/10* (2013.01)

(58) Field of Classification Search
CPC .................................................... C07D 309/10
USPC .......................... 547/200, 416; 549/200, 416
See application file for complete search history.

(56) References Cited

U.S. PATENT DOCUMENTS

| | | | |
|---|---|---|---|
| 8,618,315 B2 | 12/2013 | Gralla et al. | |
| 9,056,812 B2 | 6/2015 | Schuch et al. | |
| 9,073,826 B2 | 7/2015 | Ebel et al. | |
| 9,139,549 B2 | 9/2015 | Stork et al. | |

(Continued)

FOREIGN PATENT DOCUMENTS

| | | |
|---|---|---|
| EP | 1493737 A1 | 1/2005 |
| EP | 1516879 A1 | 3/2005 |

(Continued)

OTHER PUBLICATIONS

English Translation of International Preliminary Report on Patentability and Written Opinion for PCT/EP2014/058538 mailed Nov. 3, 2015.

(Continued)

*Primary Examiner* — T. Victor Oh
(74) *Attorney, Agent, or Firm* — Drinker Biddle & Reath LLP

(57) ABSTRACT

The invention relates to a method for producing 2-substituted 4-hydroxy-4-methyltetrahydropyrans.

22 Claims, 2 Drawing Sheets

(56) References Cited

U.S. PATENT DOCUMENTS

| | | |
|---|---|---|
| 2011/0295024 A1 | 12/2011 | Gralla et al. |
| 2014/0163117 A1 | 6/2014 | Rudenauer et al. |
| 2014/0200351 A1 | 7/2014 | Bey et al. |
| 2014/0200369 A1 | 7/2014 | Bey et al. |
| 2014/0200370 A1 | 7/2014 | Bey et al. |
| 2016/0060238 A1* | 3/2016 | Stork .................. C07D 309/10 549/416 |

FOREIGN PATENT DOCUMENTS

| | | |
|---|---|---|
| EP | 12188518.0 | 10/2012 |
| EP | 2906545 A1 | 8/2015 |
| WO | WO-2010133473 A1 | 11/2010 |
| WO | WO2011/154330 * | 12/2011 |
| WO | WO-2011154330 A1 | 12/2011 |
| WO | WO-2014060345 A1 | 4/2014 |

OTHER PUBLICATIONS

U.S. Appl. No. 14/775,834, Dienes et al.
International Search Report for PCT/EP2014/058538 mailed Jun. 24, 2014.

* cited by examiner

METHOD FOR PRODUCING 2-SUBSTITUTED 4-HYDROXY-4-METHYL-TETRAHYDROPYRANS IN A REACTOR CASCADE

CROSS-REFERENCE TO RELATED APPLICATIONS

This application is a national stage application (under 35 U.S.C. §371) of PCT/EP2014/058538, filed Apr. 28, 2014, which claims benefit of European Application No. 13165767.8, filed Apr. 29, 2013, both of which are incorporated herein by reference in their entirety.

BACKGROUND OF THE INVENTION

The present invention relates to a process for the preparation of 2-substituted 4-hydroxy-4-methytetrahydropyrans.

PRIOR ART

2-Substituted 4-hydroxy-4-methyltetrahydropyrans are valuable compounds for use as aroma chemicals. Thus, for example, the cis/trans diastereomer mixture of 2-(2-methylpropyl)-4-hydroxy-4-methyltetrahydropyran

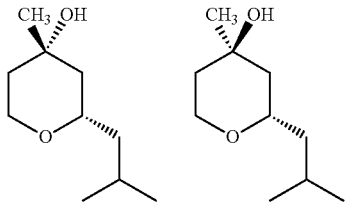

is characterized by a pleasant lily of the valley scent and is especially suitable for use as an aroma chemical, e.g. for producing fragrance compositions.

EP 1 493 737 A1 discloses a process for the preparation of mixtures of ethylenically unsaturated 4-methyl- or 4-methylenepyrans and the corresponding 4-hydroxypyrans by reaction of the corresponding aldehydes with isoprenol, where the reaction is initiated in a reaction system in which the molar ratio of aldehyde to isoprenol is greater than 1, i.e. the aldehyde is used in excess. Moreover, the document discloses the subsequent dehydration of said mixtures to give the desired ethylenically unsaturated pyrans. Suitable catalysts specified for the first reaction step are mineral acids such as hydrochloric acid or sulfuric acid, but preferably methanesulfonic acid or p-toluenesulfonic acid.

EP 1 516 879 A1 discloses a process for the preparation of ethylenically unsaturated 4-methyl- and 4-methylenepyrans by reaction of a corresponding aldehyde with isoprenol under dehydrating conditions, where the amount of water in the reactor is up to 0.25% by weight, while the conversion of the starting compound used in deficit is less than 50%. Catalysts that are specified as being suitable for this purpose are likewise mineral acids such as hydrochloric acid or sulfuric acid, but preferably methanesulfonic acid or p-toluenesulfonic acid.

WO 2010/133473 describes a process for the preparation of 2-substituted 4-hydroxy-4-methyltetrahydropyrans of the formula (I)

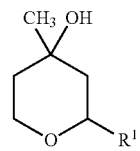

(I)

where the radical $R^1$ is a straight-chain or branched alkyl or alkenyl radical having 1 to 12 carbon atoms, an optionally alkyl-substituted cycloalkyl radical having in total 3 to 12 carbon atoms or an optionally alkyl- and/or alkoxy-substituted aryl radical having in total 6 to 12 carbon atoms, in which isoprenol (3-methylbut-3-en-1-ol) is reacted with an aldehyde of the formula $R^1$—CHO, where the reaction is carried out in the presence of water and in the presence of a strongly acidic cation exchanger.

WO 2011/154330 describes a process comparable to WO 2010/133473, where the resulting reaction mixture is supplied to a distillative work-up in a dividing-wall column or in two thermally coupled distillation columns.

The unpublished European patent application 12188518.0 describes a process for the preparation of 2-substituted 4-hydroxy-4-methyltetrahydropyrans of the general formula (I) and of 2-substituted 4-methyltetrahydropyrans of the general formula (II)

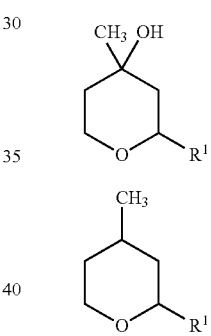

(I)

(II)

in which
$R^1$ is a straight-chain or branched $C_1$-$C_{12}$-alkyl, straight-chain or branched $C_2$-$C_{12}$-alkenyl, unsubstituted or $C_1$-$C_{12}$-alkyl and/or $C_1$-$C_{12}$-alkoxy-substituted cycloalkyl having in total 3 to 20 carbon atoms or unsubstituted or $C_1$-$C_{12}$-alkyl and/or $C_1$-$C_{12}$-alkoxy substituted aryl having in total 6 to 20 carbon atoms,
in which
a) 3-Methylbut-3-en-1-ol of the formula (III)

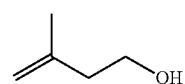

(III)

is reacted with an aldehyde of the formula (IV)

$R^1$—CHO (IV)

where $R^1$ in the formula (IV) has the meaning given above,
in the presence of an acidic catalyst, giving a reaction mixture which comprises at least one 2-substituted 4-hydroxy-4-methyltetrahydropyran of the general formula (I), at least one of the compounds (V.1), (V.2) or (V.3) and at least one dioxane compound (VI)

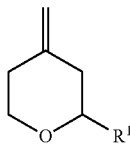
(V.1)

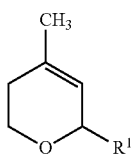
(V.2)

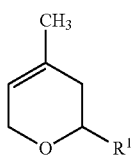
(V.3)

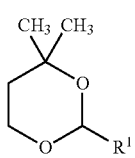
(VI)

where $R^1$ in the formula (VI) has the meaning given above, b) the reaction product from step a) is subjected to a separation, giving a fraction enriched in 2-substituted 4-hydroxy-4-methyltetrahydropyrans of the general formula (I) and a fraction which comprises at least one of the compounds (V.1), (V.2) or (V.3) and at least one dioxane compound (VI), c) the fraction which comprises at least one of the compounds (V.1), (V.2) or (V.3) and at least one dioxane compound (VI) is subjected to a hydrogenation, d) a fraction enriched in 2-substituted 4-methytetrahydropyrans (II) and a fraction enriched in at least one dioxane compound (VI) are isolated from the hydrogenation product obtained in step c).

The object of the present invention is to provide an improved process for the preparation of 2-substituted 4-hydroxy-4-methyltetrahydropyrans which permits an effective preparation on an industrial scale with the lowest possible formation of undesired by-products requiring disposal.

Surprisingly, it has now been found that this object is achieved by a procedure using at least two reactors connected in series. Specifically, it is a continuous process.

SUMMARY OF THE INVENTION

The invention provides a process for the preparation of 2-substituted 4-hydroxy-4-methyltetrahydropyrans of the general formula (I)

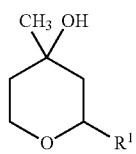
(I)

in which
$R^1$ is a straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy substituted cycloalkyl having in total 3 to 20 carbon atoms or unsubstituted or $C_1$-$C_{12}$-alkyl and/or $C_1$-$C_{12}$-alkoxy substituted aryl having in total 6 to 20 carbon atoms,
comprising a reaction of 3-methylbut-3-en-1-ol of the formula (III)

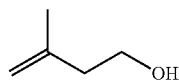
(III)

with an aldehyde of the formula (IV)

$$R^1\text{—CHO} \qquad (IV)$$

where $R^1$ in the formula (IV) has the meaning given above, in the presence of an acidic catalyst, wherein the reaction takes place in an arrangement consisting of n reactors connected in series, n being a natural number of at least 2.

DESCRIPTION OF THE INVENTION

The process according to the invention has the following advantages:
The process according to the invention permits a lower thermal stressing of the reactor contents by virtue of a lower maximum temperature and/or the avoidance of temperature peaks.
The process thus permits higher yields and/or a higher selectivity with regard to the target compounds.
A lower maximum temperature and/or the avoidance of temperature peaks are also advantageous from a safety point of view and/or permit a longer catalyst service life.
Specifically the use of a catalyst fixed-bed can additionally have an advantageous effect on the catalyst service life. Consequently, laborious start-up and shut-down operations for exchanging spent catalyst and/or for regenerating the catalyst are avoided. Moreover, the use of a catalyst fixed-bed also reduces the mechanical stress and decomposition of the catalyst.

Unless stated more precisely below, the terms "2-substituted 4-hydroxy-4-methyltetrahydropyran" and "2-(2-methylpropyl)-4-hydroxy-4-methyltetrahydropyran" within the context of the invention mean cis/trans mixtures of any composition, and also the pure conformational isomers. The terms given above furthermore refer to al enantiomers in pure form, and to racemic and optically active mixtures of the enantiomers of these compounds.

Within the context of the present invention, the expression straight-chain or branched alkyl preferably stands for $C_1$-$C_6$-alkyl and particularly preferably for $C_1$-$C_4$-alkyl. Alkyl is in particular methyl, ethyl, n-propyl, isopropyl, n-butyl, isobutyl(2-methylpropyl), sec-butyl(1-methylpropyl), tert-butyl (1,1-dimethylethyl), n-pentyl or n-hexyl. Specifically, alkyl is methyl, ethyl, n-propyl, isopropyl or isobutyl.

Within the context of the present invention, the expression straight-chain or branched alkoxy preferably stands for $C_1$-$C_6$-alkoxy and particularly preferably for $C_1$-$C_4$-alkoxy. Alkoxy is in particular methoxy, ethoxy, n-propyloxy, isopropyloxy, n-butyloxy, isobutyloxy, sec-butyloxy, tert-butyloxy, n-pentyloxy or n-hexyloxy. Specifically, alkoxy stands for methoxy, ethoxy, n-propyloxy, isopropyloxy or isobutyloxy.

Within the context of the present invention, the expression straight-chain or branched alkenyl preferably stands for $C_2$-$C_6$-alkenyl and particularly preferably for $C_2$-$C_4$-alkenyl. Besides single bonds, the alkenyl radical also has one or more, preferably 1 to 3, particularly preferably 1 or 2 and very particularly preferably one, ethylenic double bond. Alkenyl stands in particular for ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl.

Within the context of the invention, cycloalkyl refers to a cycloaliphatic radical having preferably 3 to 10, particularly preferably 5 to 8, carbon atoms. Examples of cycloalkyl groups are in particular cyclopropyl, cyclobutyl, cyclopentyl, cyclohexyl, cycloheptyl or cyclooctyl. Specifically, cycloalkyl is cyclohexyl.

Substituted cycloalkyl groups can have one or more (e.g. 1, 2, 3, 4 or 5) substituents depending on the ring size. These are preferably selected independently of one another from $C_1$-$C_6$-alkyl and $C_1$-$C_6$-alkoxy. In the case of a substitution, the cycloalkyl groups preferably carry one or more, for example one, two, three, four or five, $C_1$-$C_6$-alkyl groups. Examples of substituted cycloalkyl groups are in particular 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl and 2-, 3- and 4-isobutylcyclohexyl.

Within the context of the present invention, the expression "aryl" comprises mono- or polynuclear aromatic hydrocarbon radicals having usually 6 to 18, preferably 6 to 14, particularly preferably 6 to 10, carbon atoms. Examples of aryl are in particular phenyl, naphthyl, indenyl, fluorenyl, anthracenyl, phenanthrenyl, naphthacenyl, chrysenyl, pyrenyl, etc., and specifically phenyl or naphthyl.

Substituted aryls can have one or more (e.g. 1, 2, 3, 4 or 5) substituents depending on the number and size of their ring systems. These are preferably selected independently of one another from $C_1$-$C_6$-alkyl and $C_1$-$C_6$-alkoxy. Examples of substituted aryl radicals are 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl.

One starting material for the process according to the invention is 3-methylbut-3-en-1-ol (isoprenol) of the formula (III),

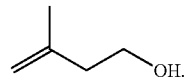

Isoprenol is readily accessible on any scale by known methods from isobutene and formaldehyde and is commercially available. No particular requirements are placed on the purity, grade or preparation process of the isoprenol to be used according to the invention. It can be used in standard commercial grade and purity in the process according to the invention. Preference is given to using isoprenol which has a purity of 90% by weight or above, particularly preferably that with a purity of 95 to 100% by weight and very particularly preferably that with a purity of 97 to 99.9% by weight or even more preferably 98 to 99.8% by weight.

A further starting material for the process according to the invention is an aldehyde of the formula (IV) $R_1$—CHO, where $R^1$ in the formula (IV) has the meaning given above.

Preferably, $R^1$ in the compounds of the formulae (I), (II) and (IV) is a straight-chain or branched $C_1$-$C_{12}$-alkyl or straight-chain or branched $C_2$-$C_{12}$-alkenyl. Particularly preferably, $R^1$ is straight-chain or branched $C_1$-$C_6$-alkyl or straight-chain or branched $C_2$-$C_6$-alkenyl. In a further preferred embodiment, $R^1$ is phenyl.

Meanings of the radical $R^1$ that are preferred according to the invention are thus for example methyl, ethyl, n-propyl, isopropyl, n-butyl, isobutyl, n-pentyl, n-hexyl or n-heptyl, preferably methyl, ethyl, n-propyl, isopropyl, n-butyl, isobutyl, very particularly preferably isobutyl(2-methylpropyl).

The radical $R^1$ is particularly preferably isobutyl or phenyl.

Aldehydes of the formula (IV) that are to be used with preference are: acetaldehyde, valeraldehyde, isovaleraldehyde, pentanal, hexanal, heptanal, benzaldehyde, citral, citronellal. According to the invention, aldehydes of the formula (IV) that are to be used with very particular preference are isovaleraldehyde and benzaldehyde, in particular isovaleraldehyde.

The reaction of the compounds (III) and (IV) takes place in an arrangement consisting of n reactors connected in series. Here, n is a natural number of at least two. According to the invention, there are 2 to 8, preferably 2, 3, 4, 5 or 6 reactors arranged one behind the other in the flow direction.

In one arrangement according to the invention, it is also possible for one or more or all of the reactors connected in series to be replaced by two or more reactors connected in parallel. This can result in a combined serial and parallel connection of (n+m) reactors. The number of reactors in the longest series of reactors connected one behind the other gives n. The number of all of the other reactors in total gives m, where m can be any desired natural number.

Preferably, the reaction takes place continuously. This means that all n reactors connected in series are each operated continuously.

In a suitable embodiment, the reaction takes place in the presence of a solvent. Optionally, for the purposes of carrying out the reaction according to the invention, the compounds of the formulae (III) and (IV), also referred to here and below as starting materials, are each supplied in the form of a mixture with a suitable solvent. Preferably, both starting materials (III) and (IV) are initially introduced in the same solvent. The solvent is preferably water or a solvent that is inert under the reaction conditions, such as, for example, tert-butyl methyl ether, cyclohexane, toluene, hexane or xylene. The specified solvents can be used on their own or in the form of mixtures. In a preferred embodiment, the reaction is carried out without the addition of an organic solvent. In a particularly preferred embodiment, the reaction takes place in the presence of water.

In a suitable embodiment of the process according to the invention, a part stream is removed between the first and last reactor in the flow direction and is fed into a reactor positioned upstream of the removal point.

In a preferred embodiment, a part stream is removed from the reactor discharge of the first and/or second reactor in the flow direction and is returned at least partially to the first reactor in the flow direction via an external recirculation. According to this embodiment, at least the first reactor in the flow direction is operated with back-mixing.

In particular, a part stream of the reactor discharge is stripped off from the first reactor and returned to the first reactor in the flow direction via an external circuit. This mode of operation is referred to here and below also as loop mode. Preferably, n here is two. The stream division for the recirculation can optionally take place before or after an interim cooling.

According to an alternative embodiment, the reaction takes place in n reactors connected one behind the other, where n is an integer of at least three. In this embodiment, a part stream is stripped off from the (n−1)th reactor and returned to the stream introduced into the first reactor via an external circuit. Consequently, the first to (n−1)th reactor together form a loop. In particular, n here is three. Here too, the stream division for the recirculation can take place optionally before or after an interim cooling.

In a particularly preferred embodiment, heat is withdrawn from the part stream before it is fed into a reactor positioned upstream of the removal point.

In an alternative embodiment of the process according to the invention, at least the first reactor in the flow direction is operated largely isothermally.

Within the context of the present invention, "operated largely isothermally" is understood as meaning that a narrow temperature interval is observed in the respective reaction zone. If the reactor is "operated largely isothermally", then within the context of the present invention this should be understood as meaning that the temperature interval ΔT in the reactor is smaller than the adiabatic temperature increase. For the temperature interval in a reactor, preferably ΔT≤12 K, particularly preferably ΔT≤10 K.

For a largely isothermic mode of operation, heat transfer surfaces are suitably arranged in the inside of the first reactor. In this case, a back-mixing in the first reactor can be dispensed with, meaning that it is particularly preferably operated in a straight pass. If a reactor is operated "in a straight pass", then this is to be understood here and below as meaning that a reactor is operated without recirculation of the reaction product in the sense of the loop mode. The mode of operation in a straight pass does not fundamentally exclude back-mixing internals and/or stirring devices in the reactor.

In a suitable embodiment, the first and second reactor in the flow direction is operated in each case largely isothermally. For this, heat transfer surfaces are suitably arranged in the inside of the two first reactors. In this way, different temperature levels can optionally be established in the reactors. In this case, it is possible to dispense with a back-mixing in the first and the second reactor, meaning that both are particularly preferably operated in a straight pass.

In a suitable embodiment, one, more or all of the streams introduced into a reactor are in each case heat-treated before entering the reactor. For this purpose, a customary heat exchanger can be used. As a rule, the stream stripped off from a reactor is subjected to interim cooling prior to entering the subsequent reactor. The heat obtained in the process can be used to heat a stream at another suitable point in the process. Corresponding processes for heat integration and/or pinch analysis are known to the person skilled in the art.

In a particularly advantageous embodiment of the process according to the invention, heat is withdrawn from the reactor discharge from at least one of the first to (n−1)th reactors before introducing it into the following reactor in the flow direction.

In a likewise preferred embodiment, at least the last reactor in the flow direction is operated without recirculation of the reactor discharge. A complete or partial product recirculation after leaving the last reactor in the flow direction is preferably not envisaged in the continuous operation.

In particular, the last reactor in the flow direction is operated essentially without back-mixing. In this case, a tubular reactor without back-mixing internals is specifically provided as the last reactor in the flow direction.

Preferably, n is 2 or 3. Particularly preferably, n is 2.

In a suitable embodiment of the process according to the invention, the reaction in at least in the last reactor in the flow direction is carried out adiabatically.

Within the context of the present invention, the term "adiabatically" is understood in the technical sense and not in the physicochemical sense. Thus, the reaction mixture, upon flowing through the reactor, generally experiences a temperature increase on account of the exothermic reaction. Adiabatic reaction implementation is understood as meaning a procedure in which the amount of heat that is released during the reaction is absorbed by the reaction mixture in the reactor and no cooling takes place by means of cooling devices. Consequently, the heat of reaction is substantially removed from the reactor with the reaction mixture. It will be appreciated that a residual amount is released into the surroundings as a result of natural heat conduction and/or radiation from the reactor. Preferably, the last reactor here is operated in a straight pass.

According to a preferred embodiment, a reactor arrangement is used for the reaction which comprises at least one fixed-bed reactor. Particular preference is given to using a reactor arrangement in which all n reactors are fixed-bed reactors.

According to one suitable embodiment, a reactor arrangement is used for the reaction which comprises at least one reactor with an internally arranged heat exchanger.

Preferably, the reaction takes place in the presence of an acidic catalyst which is selected from hydrochloric acid, sulfuric acid, methanesulfonic acid, p-toluenesulfonic acid and strongly acidic cation exchangers. In particular, the reaction is carried out in the presence of a strongly acidic cation exchanger.

Preferably, the alcohol of the formula (III) and the aldehyde of the formula (IV) are used in a molar ratio in the range from 0.7:1 to 2:1.

Preferably, the alcohol of the formula (III) and the aldehyde of the formula (IV) are reacted in the presence of at least 3% by weight, particularly preferably at least 5% by weight, of water. The alcohol of the formula (III) and the aldehyde of the formula (IV) are reacted for example in the presence of 3% by weight to 15% by weight of water, preferably from 5% by weight to 12% by weight. The percent by weight given above are based here on the amount of the reaction mixture, consisting of the components of the formulae (III) and (IV) and also water.

As a rule, the reaction of the alcohol of the formula (III) is carried out with the aldehyde of the formula (IV) in the presence of about at least 10 mol % of water, where the amount of water is based on the amount of the starting material optionally used in deficit, or in the case of an equimolar reaction on the quantitative amount of one of the two starting materials. Above the stated value, the amount of water can be chosen freely and is limited only by processing or cost aspects. Water can also be used in a large excess, for example in 10- to 100-fold excess, or even more. Preferably, a mixture is prepared from the alcohol of the formula (III) and the aldehyde of the formula (IV) with the selected amount of water, meaning that the added water remains dissolved in the mixture, i.e. a two-phase system is not present.

In a suitable embodiment, the starting materials are reacted in the presence of at least 25 mol %, preferably at least 50 mol %, of water. For example, the starting materials are reacted in the presence of 25 to 150 mol %, preferably from 40 to 150 mol %, particularly preferably from 50 to 140 mol %, in particular from 50 to 80 mol %, of water. Here, the amount of water used refers to the quantitative amount of the starting material optionally used in deficit or, in the case of an equimolar reaction, to the quantitative amount of one of the two.

In a suitable embodiment of the process according to the invention, the reaction is carried out at a temperature in the range from 0° C. to 70° C., preferably in the range from 20° C. to 70° C., particularly preferably in the range from 20° C. to 60° C.

In a likewise suitable embodiment of the process according to the invention, the reaction is carried out at a pressure in the range from 1 bar to 15 bar.

If the reaction mixture reacted in one of the reactors connected downstream of the first reactor (i.e. the second to n-th reactor) has fractions of starting materials which are too low in order to maintain the desired temperature in the reactor via the heat of reaction that is formed, a heat treatment of the reactor (or individual reaction zones) may also be necessary. The heat treatment can take place analogously to the above-described dissipation of the heat of reaction by heating an external circulation stream or by means of internal heating via heat exchange surfaces. In one suitable embodiment, the dissipated heat of reaction from at least one of the preceding reactors can be used for the heat treatment.

The withdrawn heat of reaction can optionally also be used for heating the feed streams of the reactors. For this, e.g. the starting material stream in the first reactor can be mixed at least partially with an external circulation stream of this reactor and the combined streams can then be fed into the first reactor. Furthermore, the feed streams can be fed into one, more or all of the second to n-th reactors with a circulation stream from the respective reactor jointly into this reactor. Furthermore, the starting material stream and/or another feed stream can be heated with the help of a heat exchanger which is operated using withdrawn heat of reaction.

In one embodiment, an additional thorough mixing can take place in at least one of the reactors used. An additional thorough mixing is advantageous particularly if the reaction takes place with long residence times of the reaction mixture. Both static and also dynamic mixing devices are suitable. Suitable mixing devices are sufficiently known to the person skilled in the art. For the purposes of thorough mixing, the feed streams fed into the reactors can preferably be fed into the respective reactors by suitable mixing devices, such as nozzles. For thorough mixing, (part) streams from the respective reactor which are conveyed in an external circuit can likewise preferably be used, as described above as loop mode.

The loop mode described above is particularly advantageously suitable for regulating the reaction temperature and the heat transfer between reaction medium, apparatus walls and surroundings. A further option for controlling the heat balance consists in regulating the entry temperature of the starting material and/or of the respective feed stream. Thus, a lower temperature of the entering feed generally leads to an improved dissipation of the heat of reaction. As the catalyst activity diminishes, the entry temperature chosen can be higher in order to achieve a higher rate of reaction and to thereby compensate for the diminishing catalyst activity. Thus, the service life of the catalyst used can be advantageously increased.

The first part stream is generally returned to the reaction system chemically unchanged. If desired, the temperature and/or the pressure can be adjusted to the desired values prior to the recirculation. The first part stream can be fed into the reactor, from which it was removed, together with the respective feed stream or separately therefrom. The quantitative weight ratio of first part stream (recirculation stream) fed into the reactor to the respective feed stream is preferably in a range from 1:1 to 50:1, particularly preferably in a range from 2:1 to 30:1, in particular in the range from 5:1 to 20:1.

In a second variant, the reaction takes place in the presence of a strongly acidic cation exchanger. Here, the term strongly acidic cation exchanger is understood as meaning a cation exchanger in the $H^+$ form which has strongly acidic groups. The strongly acidic groups are generally sulfonic acid groups. The acidic groups are generally bonded to a polymer matrix, which may be e.g. gel-like or macroporous. A preferred embodiment of the process according to the invention is accordingly characterized in that a strongly acidic cation exchanger having sulfonic acid groups is used. Suitable strongly acidic cation exchangers are described in WO 2010/133473 and WO 2011/154330, to which reference is made here in its entirety.

Of suitability for the use are strongly acidic ion exchangers (such as e.g. Amberlyst, Amberlite, Dowex, Lewatit, Purolite, Serdolit), which are based on polystyrene and which comprise copolymers of styrene and divinylbenzene as carrier matrix with sulfonic acid groups in $H^+$ form, and also ion exchanger groups functionalized with sulfonic acid groups ($-SO_3H$). The ion exchangers differ in the structure of their polymer backbones, and a distinction is made between gel-like and macroporous resins. In a specific embodiment, a perfluorinated polymeric ion exchanger resin is used. Resins of this type are sold e.g. under the name Nafion® by DuPont. One example of such a perfluorinated polymeric ion exchanger resin which may be mentioned is Nafion® NR-50.

Commercially available strongly acidic cation exchangers suitable for the reaction are known for example under the trade names Lewatit® (Lanxess), Purolite® (The Purolite Company), Dowex® (Dow Chemical Company), Amberlite® (Rohm and Haas Company), Ambertyst™ (Rohm and Haas Company). Preferred strongly acidic cation exchangers are: Lewatit® K 1221, Lewatit® K 1461, Lewatit® K 2431, Lewatit® K 2620, Lewatit® K 2621, Lewatit® K 2629, Lewatit® K 2649, Amberlite® FPC 22, Amberlite® FPC 23, Amberlite® IR 120, Amberlyst™ 131, Amberlyst™ 15, Amberlyst™ 31, Amberlyst™ 35, Amberlyst™ 36, Amberlyst™ 39, Amberlyst™ 46, Amberlyst™ 70, Purolite® SGC650, Purolite® C100H, Purolite® C150H, Dowex® 50X8, Serdolit® red and Nation® NR-50.

The strongly acidic ion exchanger resins are generally regenerated with hydrochloric acid and/or sulfuric acid.

In a specific embodiment, the 3-methylbut-3-en-ol (III) and the aldehyde (IV) are reacted in the presence of a strongly acidic cation exchanger and in the presence of water. In principle, the reaction mixture can already comprise small amounts of water which can be released as a result of the dehydrogenation of the process product of the formula (I) as possible secondary reaction. According to a specific embodiment, water can also additionally be added to the reaction mixture as well as isoprenol (III) and the aldehyde of the formula (IV) and some water from the reaction.

Preferably, the alcohol of the formula (III) and the aldehyde of the formula (IV) are reacted in the presence of at least 3% by weight, particularly preferably at least 5% by weight, of water. The alcohol of the formula (III) and the aldehyde of the formula (IV) are reacted for example in the presence of 3% by weight to 15% by weight of water, preferably from 5% by weight to 12% by weight. The stated above percent by weight here are based on the total amount of the reaction mixture consisting of the components of the formulae (III) and (IV) and also water.

Above the stated value, the amount of water can be chosen freely and is limited, if at all, only by processing or cost aspects and it is entirely possible for it to be used in a large excess, for example in 5- to 15-fold excess or even more. Preferably, a mixture of isoprenol (III) and the aldehyde of the formula (IV), preferably isovaleraldehyde, is prepared with the amount of water to be added such that the added water remains dissolved in the mixture of isoprenol and the aldehyde, i.e. a two-phase system is not present.

Usually, within the context of this embodiment of the process according to the invention, the starting materials isoprenol (III) and the aldehyde of the formula (IV) are reacted in the presence of at least 25 mol %, preferably at least 50 mol %. For example, the starting materials are reacted in the presence of from 25 to 150 mol %, preferably from 40 to 150 mol %, particularly preferably from 50 to 140 mol %, in particular from 50 to 80 mol %, of water. In this connection, the amount of water used refers to the quantitative amount of the starting material optionally used in deficit or, in the case of an equimolar reaction, to the quantitative amount of one of the two.

For the reaction of isoprenol (III) with the aldehyde (IV), the stated starting materials and optionally the added water can be brought into contact with the acidic cation exchanger. Preferably, Isoprenol (III), aldehyde (IV) and optionally the added water are used in the form of a mixture. The specified starting materials, i.e. isoprenol (III) and the aldehyde (IV) and the water to be used in the above amount can be brought into contact with one another and/or mixed in any desired order.

The amount of strongly acidic cation exchanger is not critical and can be chosen freely within wide limits taking into consideration the economic and processing aspect. The reaction can accordingly be carried out both in the presence of catalytic amounts and also in the presence of large excesses of the strongly acidic cation exchanger. The specified strongly acidic cation exchangers can be used either individually or in the form of mixtures.

The space velocity is for example in the range from 50 to 2500 mol per $m^3$ of catalyst and h, preferably in the range from 100 to 2000 mol per $m^3$ of catalyst and h, in particular in the range from 130 to 1700 mol per $m^3$ of catalyst and h, where the quantitative amount in mol refers to the starting material of the formula (IV).

The reaction in the presence of a strongly acidic cation exchanger can if desired also additionally be carried out in the presence of a solvent that is inert under the reaction conditions. Suitable solvents are, for example, tert-butyl methyl ether, cyclohexane, decalin, hexane, heptane, naphtha, petroleum ether, toluene or xylene. The specified solvents can be used on their own or in the form of mixtures with one another. Preferably, the reaction is carried out in the presence of a strongly acidic cation exchanger without the addition of an organic solvent.

Preferably, the reaction of isoprenol (III) with the selected aldehyde (IV) is carried out in the presence of water and in the presence of a strongly acidic cation exchanger at a temperature in the range from 0 to 70° C., particularly preferably at a temperature in the range from 20 to 70° C. and in particular at a temperature in the range from 20 to 60° C. This is the temperature of the reaction mixture.

The work-up of the reaction product for obtaining the product of value can take place by customary methods known to the person skilled in the art. Preferably, the work-up of the reaction mixture comprises at least one distillation step. The reaction product can be separated in a known manner by distillation or rectification in order to thus obtain the product of value. For example, the work-up can take place analogously to the method described in WO 2011/154330.

DESCRIPTION OF THE FIGURES

The process according to the invention is explained in more detail by reference to FIGS. 1 to 3 below without limiting it to these embodiments.

In FIGS. 1 to 3 the following reference numerals are used:
1 (Main) reactor
2 Cooling unit
3 (Secondary) reactor
4 (Intermediate) cooling unit
5 Pump
6 Reactor
7 Cooling unit
8 Separating column
A Isoprenol stream
B Aldehyde stream
C Water
D Recirculation stream
E Starting material The process according to the invention can be carried out with at least one main reactor, preferably 1 to 2 main reactors, in cascade form. The main reactors can be operated in parallel or in series, preferably in series, and optionally with interim cooling. Here, the procedure can take place, for example, in the back-mixed reactor system or in isothermal mode. In the back-mixed reactor system, an of the circulation stream of the main reactor part can be back-mixed and cooled or each main reactor separately can be back-mixed and cooled by its own circulation stream and/or intermediate cooling can take place after each main reactor. The division into two or more beds, optionally also with interim cooling, can also be implemented in one apparatus.

After emerging from the main reactor part of the reaction, at least one secondary reactor follows, preferably 1 to 2 secondary reactors. These can be operated in a straight pass (isothermally or back-mixed), in parallel or in series. Preferably, they are connected in series and operated in a straight pass without back-mixing.

Figure 1:
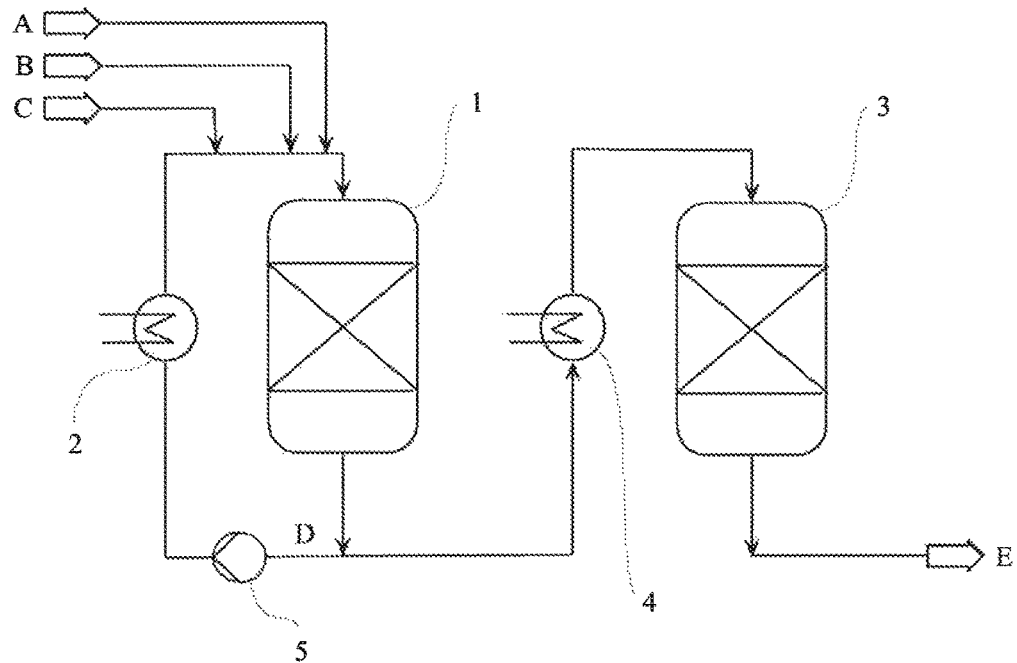
FIG. 1 shows an embodiment of the process according to the invention with a main reactor with recirculation stream and a secondary reactor.

FIG. 1 shows a suitable embodiment of a suitable two-stage reactor cascade with a main reactor (1) and a secondary reactor (3).

The three starting material streams isoprenol (A), aldehyde (B) and water (C) are introduced into the reactor (1) via three feeds. A discharge from the reactor (1) is removed via a line and the pump (5) and is divided into two part streams. A recirculation stream (D) is fed to the main reactor (1) via the cooling unit (2) together with the starting material streams (A), (B) and (C). A feed stream is passed via a cooling unit (4) to the second reactor (3). The starting material (E) is removed directly from the secondary reactor (3) as discharge and optionally fed to a work-up stage.

In this embodiment, both reactors are preferably configured as fixed-bed reactors. The main reactor (1) is operated in loop mode, whereas the secondary reactor is operated in a straight pass. In the arrangement shown in FIG. 1, the main reactor (1) and the secondary reactor (3) are connected in series such that the temperature profile above the catalyst bed can be adjusted via a back-mixing in the main reactor system. As a result, a large temperature increase at the start of the reaction can be prevented.

Figure 2:
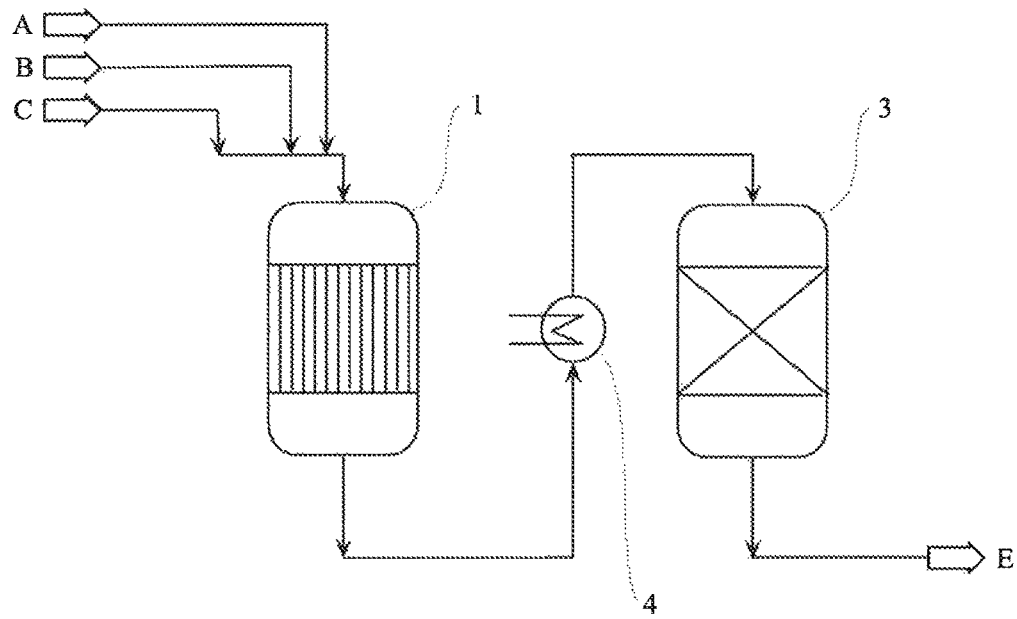
FIG. 2 shows an embodiment of the process according to the invention with a main reactor with integrated heat exchanger and a secondary reactor.

FIG. 2 shows an alternative embodiment of a suitable two-stage reactor cascade with a main reactor (1) and a secondary reactor (3). Instead of the recirculation, an isothermal reaction procedure is achieved via a heat exchanger integrated into the reactor (1).

The three starting material streams isoprenol (A), aldehyde (B) and water (C) are introduced into the reactor (1). A discharge from the reactor (1) is removed and is supplied as feed stream to the second reactor (3) via a cooling unit (4). The starting material (E) is removed directly as discharge from the secondary reactor (3) and optionally fed to a work-up stage. The main reactor is equipped with integrated heat exchange surfaces, whereas the secondary reactor (3) is designed as a simple fixed-bed reactor. Both reactors are operated in this embodiment in a straight pass. The isothermal reaction procedure shown in FIG. 2 avoids undesired temperature peaks.

Figure 3:
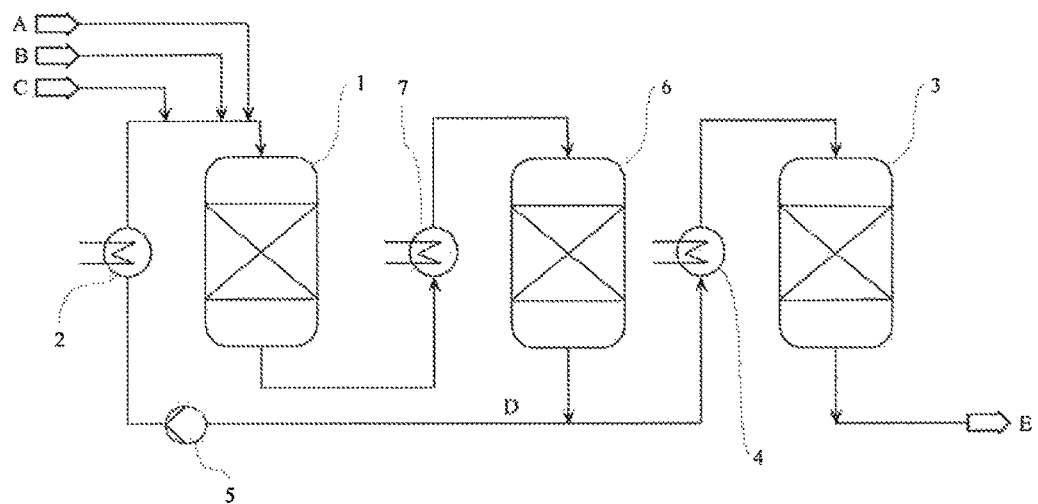
FIG. 3 shows an embodiment of the process according to the invention with two reactor stages with recirculation stream and a secondary reactor.

FIG. 3 shows one suitable embodiment of a three-stage reactor cascade with two main reactors (1), (6) and a secondary reactor (3).

The three starting material streams isoprenol (A), aldehyde (B) and water (C) are introduced into the reactor (1) via three feeds. A discharge from the reactor (1) is removed and is fed as feed stream to the second reactor (6) via a cooling unit (7). A discharge is removed from the reactor (6) via a line and the pump (5) and is divided into two part streams. A recirculation stream (D) is returned to the main reactor (1) together with the starting material streams (A), (B) and (C) via the cooling unit (2). A feed stream is fed to the third reactor (3) via a cooling unit (4). The starting material (E) is removed directly as discharge from the secondary reactor (3) and optionally fed to a work-up stage.

In this embodiment, all three reactors are preferably configured as fixed-bed reactors. The main reactors (1) and (6) are operated together in loop mode, whereas the secondary reactor (3) is operated in a straight pass. In the arrangement shown in FIG. 3, the main reactors (1), (6) and the secondary reactor (3) are connected in series such that the temperature profile above the catalyst bed can be adjusted via a back-mixing in the main reactor system and an interim cooling between the first and second main reactor. As a result, temperature peaks in both reactors can be effectively prevented.

EXAMPLES

Example 1

Continuous Process

An apparatus consisting of a main reactor and a secondary reactor consisting of three individual reactors was used. The main reactor used was a jacketed reactor made of RA4 without heating medium for an adiabatic procedure with a length of 150 cm and an internal diameter of 2.6 cm. The secondary reactor used was three jacketed reactors made of RA4, each with a length of 150 cm, an internal diameter of 1.0 cm and heated at respectively 30° C., 40° C. and 50° C.

The apparatus was filled with a total of 328 g of the strongly acidic cation exchanger Amberlyst™ 131. The main reactor was in this case filled with 230 g (305 ml), the secondary reactors each with 32.5 g (44 ml), of the cation exchanger. The cation exchanger was washed prior to use firstly several times with water, then once with methanol and finally with water so as to be methanol-free. The system was conditioned by introducing a mixture of pyranol:water in a mass ratio of 95:5. The main reactor was then operated back-mixed with a recirculation stream of 2000 g/h, the recirculated stream being cooled to a temperature of 25° C. before reentering the main reactor. The secondary reactor was operated in a straight pass to complete conversion.

After conditioning the cation exchanger to the stated pyranol/water mixture, a mixture of isovaleraldehyde:isoprenol:water in a mass ratio of 45:50:5 was introduced at 25° C. and in a total quantitative stream of 100 g/h. This gave a crude product with an exit temperature from the last secondary reactor of 50° C. in a yield of 76% and with a selectivity of 77.6% based in each case on isovaleraldehyde with the following composition:
Isovaleraldehyde: 1.03 GC % by weight,
Isoprenol: 3.6 GC % by weight,
Dihydropyran isomers: 8.69 GC % by weight,
1,3-Dioxane: 5.56 GC % by weight,
Acetal: 0.57 GC % by weight,
trans-Pyranol: 18.26 GC % by weight,
cis-Pyranol: 50.08 GC % by weight,
Water: 6.8% by weight (according to Karl Fischer).

The invention claimed is:
1. A process for the preparation of a 2-substituted 4-hydroxy-4-methyltetrahydropyran of the formula (I)

in which
R¹ is a straight-chain or branched $C_1$-$C_{12}$-alkyl, straight-chain or branched $C_2$-$C_{12}$-alkenyl, unsubstituted or $C_1$-$C_{12}$-alkyl and/or $C_1$-$C_{12}$-alkoxy substituted cycloalkyl having in total 3 to 20 carbon atoms or unsubstituted or $C_1$-$C_{12}$-alkyl and/or $C_1$-$C_{12}$-alkoxy substituted aryl having in total 6 to 20 carbon atoms,
comprising reacting 3-methylbut-3-en-1-ol of the formula (III)

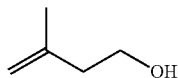

(III)

with an aldehyde of the formula (IV)

 (IV)

where R¹ in the formula (IV) has the meaning given above,
in the presence of an acidic catalyst, wherein the reaction takes place in an arrangement consisting of n reactors connected in series, n being a natural number from 2 to 8;
wherein a part stream is removed between the first and last reactor in the flow direction and is fed into a reactor positioned upstream of the removal point.

2. The process according to claim 1, wherein the reaction takes place continuously.

3. The process according to claim 1, wherein the reaction takes place in the presence of a solvent.

4. The process according to claim 1, wherein a part stream is removed from the reactor discharge of the first and/or second reactor in the flow direction and is returned at least partially to the first reactor in the flow direction via an external recirculation.

5. The process according to claim 4, wherein the part stream of the reactor discharge is stripped off from the first reactor and is returned to the first reactor in the flow direction via an external circuit.

6. The process according to claim 1, wherein heat is withdrawn from the part stream before it is fed into a reactor positioned upstream of the removal point.

7. The process according to claim 1, wherein at least the first reactor in the flow direction is operated isothermally.

8. The process according to claim 1, wherein the first and second reactor in the flow direction is operated in each case isothermally.

9. The process according to claim 1, wherein the (n−1)th reactor in the flow direction is operated isothermally.

10. The process according to claim 1, wherein heat is withdrawn from the reactor discharge from at least one of the first to (n−1)th reactors before introducing it into the following reactor in the flow direction.

11. The process according to claim 1, wherein at least the last reactor in the flow direction is operated without recirculation of the reactor discharge.

12. The process according to claim 1, wherein n is 2 or 3.

13. The process according to claim 1, wherein the reaction at least in the last reactor in the flow direction is carried out adiabatically.

14. The process according to claim 1, wherein a reactor arrangement is used for the reaction which comprises at least one fixed-bed reactor.

15. The process according to claim 1, wherein a reactor arrangement is used for the reaction which comprises at least one reactor with an internally arranged heat exchanger.

16. The process according to claim 1, wherein R¹ is isobutyl or phenyl.

17. The process according to claim 1, wherein the reaction takes place in the presence of an acidic catalyst which is selected from the group consisting of hydrochloric acid, sulfuric acid, methanesulfonic acid, p-toluenesulfonic acid and strongly acidic cation exchangers.

18. The process according to claim 13, wherein the reaction is carried out in the presence of a strongly acidic cation exchanger.

19. The process according to claim 1, wherein the alcohol of the formula (III) and the aldehyde of the formula (IV) are used in a molar ratio in the range from 0.7:1 to 2:1.

20. The process according to claim 1, wherein the alcohol of the formula (III) and the aldehyde of the formula (IV) are reacted in the presence of 3% by weight to 15% by weight of water based on the amount of the reaction mixture consisting of the components of the formulae (III) and (IV) and water.

21. The process according to claim 1, wherein the reaction is carried out at a temperature in the range from 0° C. to 70° C.

22. The process according to claim 1, wherein the reaction is carried out at a pressure in the range from 1 bar to 15 bar.

* * * * *